United States Patent

Pilz et al.

[19]

[11] Patent Number: 6,044,295
[45] Date of Patent: Mar. 28, 2000

[54] IMPLANTABLE MULTI-FUNCTION MEDICAL DEVICE

[75] Inventors: Juergen Pilz; Juergen Mueller, both of Berlin; Roland Staub, Berggiesshuebel; Gerd Fehrmann, Pirna, all of Germany

[73] Assignee: Litronik Batterietechnologie GmbH & Co., Pirna, Germany

[21] Appl. No.: 09/061,043

[22] Filed: Apr. 16, 1998

[30] Foreign Application Priority Data

Apr. 16, 1997 [DE] Germany .................... 197 16 969

[51] Int. Cl.[7] .................... A61N 1/378; A61N 1/39
[52] U.S. Cl. ......................... 607/4; 607/5; 607/29
[58] Field of Search ................ 607/4, 5, 9, 29

[56] References Cited

U.S. PATENT DOCUMENTS

| | | |
|---|---|---|
| 3,655,585 | 4/1972 | Dey et al. . |
| 3,871,383 | 3/1975 | Lee . |
| 3,947,289 | 3/1976 | Dey et al. . |
| 4,096,866 | 6/1978 | Fischell . |
| 4,134,408 | 1/1979 | Brownlee et al. . |
| 4,310,609 | 1/1982 | Liang et al. . |
| 4,391,729 | 7/1983 | Liang et al. . |
| 4,416,282 | 11/1983 | Saulson et al. . |
| 4,590,941 | 5/1986 | Saulson et al. . |
| 5,114,811 | 5/1992 | Ebel et al. . |
| 5,191,884 | 3/1993 | Gilli et al. .................... 607/5 |
| 5,372,605 | 12/1994 | Adams et al. ................ 607/5 |
| 5,591,212 | 1/1997 | Keimel . |
| 5,614,331 | 3/1997 | Takeuchi et al. . |
| 5,773,961 | 6/1998 | Cameron et al. ............ 607/5 |

FOREIGN PATENT DOCUMENTS

| | | |
|---|---|---|
| 0638946 | 2/1995 | European Pat. Off. . |
| 0777286 | 6/1997 | European Pat. Off. . |
| 4438784 | 4/1995 | Germany . |
| 94/02202 | 2/1994 | WIPO . |

OTHER PUBLICATIONS

New Rate Lithium/VanadiumPentoxideCell for Implantable Medical Devices, by R. J. Horning et al. Progress In Batteries & Solar Cells, vol. 4, 1982, pp. 97–102.

*Primary Examiner*—William E. Kamm
*Assistant Examiner*—Carl H. Layno
*Attorney, Agent, or Firm*—Venable; George H. Spencer; Robert Kinberg

[57] ABSTRACT

An implantable multi-function medical device, having a first therapy assembly that has a small current requirement and a second therapy assembly that has a large current requirement. The device further has a first battery component that is adapted to a consumer having a low current requirement, and a second battery component that is adapted to a consumer having a large current requirement, and a switching device which connects the second battery component only to the second therapy assembly until a control signal is emitted, which indicates that a predetermined voltage level of the first battery component has not been met, or that an internal resistance has been exceeded, but, as of this time, the switching device connects the second battery component to the first therapy assembly.

15 Claims, 2 Drawing Sheets

IMPLANTABLE MULTI-FUNCTION MEDICAL DEVICE

CROSS-REFERENCE TO RELATED APPLICATION

This application claims the priority of patent application Ser. No. P 197 16 969.4, filed Apr. 16, 1997, in the Federal Republic of Germany, the subject matter of which is incorporated herein by reference.

BACKGROUND OF THE INVENTION

The invention relates to an implantable, multi-function medical device, particularly a combination cardiac pacemaker/defibrillator, in which different therapeutic functions place different load requirements on the battery. This can relate to the available current intensity or the available power.

In particular, a first function may require a low current in the $\mu A$ range over extended periods of time, and a second function may require a short-time pulse current in the Ampere range over several seconds for certain events occurring at irregular intervals.

Known energy sources for meeting such requirements are commercially available and are implemented in the field of human medicine. These energy sources are corresponding electrochemical systems which, depending on the structural design, are capable of emitting current intensities in ranges between $10^{-6}$ A and almost 10 A.

The electrochemical system of lithium/silver vanadium oxide is particularly suited for fulfilling these conditions; details about the system are given in U.S. Pat. Nos. 4,310,609, 4,391,729 and 5,114,811, as well as European Patent Application EP 0 638 946 A2.

Batteries using the lithium/vanadium system are also known: refer to U.S. Pat. Nos. 3,655,585 and 3,947,289 and R. J. Horning et al, New Rate Lithium/VanadiumPentoxideCell for Implantable Medical Devices, Progress In Batteries & Solar Cells, Vol. 4, 1982, pages 97–102.

A further practical system that comprises lithium, manganese oxide, lead oxide and chromium oxide is described in DE 4 438 784 A1, and is the subject of EP 0 777 286 B1.

Known batteries contain metal-oxide and lithium electrodes in an organic electrolyte. Such electrochemical systems have a maximum load of 30 mAcm$^2$. Output powers in the order of magnitude of 10-W pulses can thus only be attained by battery constructions having a large surface area. Because of the large proportion of passive components in such batteries, the energy density in Wh/l and Wh/kg is relatively low.

A disadvantage shared by all of the aforementioned electrochemical systems is that they possess a relatively low energy density in Wh/kg and Wh/l because of the power requirements in different load ranges. Consequently, either the mass and volume of the battery are very high for an acceptable service life, or small and lightweight devices must be replaced relatively frequently.

U.S. Pat. No. 4,134,408 discloses a power-supply arrangement for an implantable pacemaker, which includes, in addition to the conventional (primary) battery, means for temporary external energy supply, and an associated (secondary) battery that has a low capacity and can be charged externally, and can then supply the pacemaker for a limited time in order to preserve the primary battery.

U.S. Pat. No. 5,591,212 discloses a so-called hybrid battery arrangement for an implantable pulse generator, especially an implantable defibrillator; in addition to the battery, the arrangement includes a capacitor that has a high energy density and is selectively connected to the battery for ensuring the supply of the control electronics of the device during operating phases requiring a large amount of current. A similar solution for a pacemaker had already been described in U.S. Pat. Nos. 4,416,282 and 4,590,941. These documents also teach the provision of an emergency backup battery, which can be activated in the event of a sudden voltage drop of the primary battery.

Providing a costly and voluminous high-capacity capacitor solely for the purpose of current management (without the capacitor being able to supply additional energy) is, in the end, as equally unsatisfactory as providing an emergency battery that, as such, permits neither an adaptation to different current requirements nor a significant extension of the service life.

With reference to older, two-battery arrangements for pacemakers, PCT Application WO 94/02202 describes an implantable cardioverter/defibrillator in which special batteries are provided for observation functions, on the one hand, and for emitting stimulation energy, on the other hand. These batteries are optimized to have a long service life with very low current intensities, on the one hand, and to provide a high peak current and an extremely low self-discharging, on the other hand. In particular, a pair of lithium/iodine batteries and lithium/vanadium pentaoxide batteries is used. This device has only one therapeutic function; furthermore, the inflexible allocation of the battery functions is unsatisfactory.

SUMMARY OF THE INVENTION

It is therefore the object of the invention to provide an implantable, multi-function medical device that has a significantly longer service life with respect to its base function, which has a low current consumption. This is particularly relevant for the mass and/or the volume of the used battery arrangement.

This object is accomplished by a multi-function device having a first battery component that is adapted to a consumer therapy assembled with a low current requirement, and a second battery component that is adapted to a consumer therapy assembled with a large current requirement, a sensor that has a measuring device for detecting a measured value that is characteristic for the residual energy of the first battery component, taking into consideration the current and/or voltage requirement of the second therapy assembly, a measuring device that is connected on the input side to the sensor for emitting a control signal when the residual energy of the first battery component no longer suffices for low-current operation of the first therapy assembly, and a switching device that is connected to the output of the measuring device, and connects the second battery component only to the second therapy assembly until the control signal is emitted, which indicates that the available residual energy is less than the predetermined residual energy of the first battery component, but as of this time the switching device connects the second battery component to the first therapy assembly.

The invention includes the teaching of using two different battery components for separately performing the tasks of supplying a low (constant) current for a first therapy component and a high (pulse) current for a second therapy component for most of the service life. In the process, the capacity and power of the assemblies are conceptualized such that the medical device can be reliably operated to perform its essential functions over its service life. In this manner, the structural volume that is necessary overall for the energy requirement for such a device can be optimized.

The first therapy component is automatically switched to the second battery component at the time when the first battery component for the function requiring low current intensities has been depleted to the point that a lower voltage value is not met, or an upper internal-resistance value is exceeded. Up to this point, the second battery component has only occasionally supplied high current pulses, and—under normal conditions of use—is for the most part oversized in its capacity. As of the switching point, the second battery component supplies the necessary current for the first therapy component (constant current), preferably in addition to the further supply of the second therapy component (supply of the short-time high-current pulses). Depending on the concrete embodiment, the second battery component can perform this task alternatingly with the first battery (especially in the recovery phases of the battery), or continuously by itself.

In an advantageous embodiment, through the combination of a first battery, specifically an Li/I battery having a high energy density ($\geq 700$ Wh/l, $\geq 170$ Wh/kg) for the low-current range, and a second battery, which has a low energy density but a high power density ($\geq 300$ Wh/l, $\geq 130$ Wh/kg) for pulse operation, the two batteries are stressed in their specific optimal current-density ranges for the operating period of several years. In a preferred embodiment of the invention, the batteries are hermetically sealed.

Depending on the application, the capacity concept of the Li/I battery can be such that the battery is depleted after 4, 5, 6 or more years. The concrete embodiment of the combination of the two batteries is solely dependent on the requirements of the respective application. The nominal voltage of the first battery is preferably 3 or 6 Volts.

A crucial feature for the reliable and safe function of the battery arrangement is an electronic circuit which, up to the switching time, ensures that all of the high-current pulses are only handled by the second battery, and the first battery covers the entire low-current requirement.

In a practical embodiment, the circuit is configured such that the two batteries are connected to the two inputs of a current-supply element, whose output supplies a low-current control circuit, and the second battery is additionally connected to the high-current circuit that is connected by way of control lines to the control circuit. The current-supply element is formed by a capacitor switched in parallel to the first battery, a voltage-sensor comparison unit (voltage comparator), a logic element, two electronic switches and a voltage regulator. In this embodiment, the two inputs of the current-supply element for the control circuit are respectively connected by way of an electronic switch to the input of the voltage regulator, whose output simultaneously represents the output of the current-supply element, with the electronic switches being actuated by the input connected to the first battery, by way of the voltage comparator and a logic element disposed one behind the other.

The control circuit particularly comprises a pacemaker circuit and a control for the high-current circuit. An input of this control circuit is connected to the output of the voltage comparator.

The high-current circuit is activated by the control circuit as needed (for example, for charging the shock capacitor in an implantable defibrillator), and is otherwise switched off, that is, it is in the non-operative state, during which it receives no current from the second battery.

In a first operating phase, the control circuit is supplied by the first battery; the input of the voltage regulator in the current-supply element is connected by way of the electronic switch to the first battery, while the second electronic switch is open. If the voltage of the first battery drops below a fixed, predetermined, battery-specific value because of discharging, the voltage comparator and, by way of the logic element, the two electronic switches switch; the input of the voltage regulator is now connected to the second battery, and the first electronic switch is open. In this case, the control circuit is supplied by the second battery. An increase in the internal resistance above a predetermined value can be used as a switching criterion, and a current-measuring circuit can be used for detection. A measured value is determined that indicates that a residual charge value of the battery component has been attained; if this value is not met, the battery component is no longer capable of maintaining the first assembly in a ready state.

In the simplest embodiment, the logic element includes only a circuit for opposite-phase actuation of the electronic switches. After the increase in the voltage of the first battery, which is unstressed and recovering after the switch to the second battery, the circuit returns to its initial state, causing the voltage to begin falling again, etc. In this case, the control circuit (i.e., the first therapy assembly) is alternatingly supplied by the first and second batteries. This can be prevented with a bistable element in the logic element. As of the switching point, the control circuit is supplied solely by the second battery.

At the same time, the control circuit is supplied with information regarding the attainment of the switching point, which information can be taken into consideration in the determination of the ERI (Elective Replacement Indication).

In the solution according to the invention, the replacement of the implant can be postponed in comparison to conventional solutions, because a reserve energy, which is typically substantial, is provided.

Monitoring the discharge state of the second battery with hardware and/or software suffices to determine the ultimate ERI point. The ERI point is attained when the second battery is also depleted to the point that it only contains exactly enough energy for reliable operation of the implant during a defined time span (including a defined number of maximum energy shocks in a defibrillator).

So that the postponed ERI point can also be determined, the following are preferably provided: a further sensor having a further measuring device for detecting a measured value that is characteristic for the residual energy of the second battery component, taking into consideration the current and/or voltage requirement of the first therapy assembly; a measuring device that is connected on the input side to the further sensor for emitting a further control signal when the residual energy of the second battery component only suffices for low-current operation of the first therapy assembly for a limited amount of time; and a telemetry device that is connected to the output of the further measuring device and transmits a telemetry signal to a receiver located outside of the patient's body, the signal being influenced by the further control signal.

If the output signal of the further measuring device is combined with the signal of the first measuring device such that the telemetry signal is influenced, in different ways, by both the control signal and the further control signal, the switching points of the two measuring devices can be controlled externally. By conducting an appropriate query with a programming device, the attending physician is informed of the shutoff time of the first battery. Depending on the number of defibrillation shocks that the patient requires, a considerable energy reserve is still available, which significantly lengthens the operating period of the low-energy assembly, so that it does not become necessary in any case to re-implant the device only because the battery that can be stressed with a low current fails. A further telemetry signal that has been transmitted in combination indicates the end of the foreseeable operating period of the second battery.

In defibrillators having an additional pacemaker component, the first and second batteries often have different terminal voltages. In such a case, it is advantageous if a voltage transformer is provided whose transmission ratio can be switched by the control signal such that the transmission ratio essentially corresponds to the ratio of the terminal voltage of the first battery component to the supply voltage of the first therapy assembly when the first therapy assembly is connected to the first battery component, and the transmission ratio corresponds to the ratio of the terminal voltage of the second battery component to the supply voltage of the first therapy assembly when the first therapy assembly is connected to the second battery component. This ensures that, after the battery has been switched, another supply voltage can also be used for operation of the low-energy assembly without substantial energy losses if the efficiency remains basically unchanged.

BRIEF DESCRIPTION OF THE DRAWINGS

These and other features and advantages of the invention will be further understood from the following detailed description of the preferred embodiment with reference to the accompanying drawings, in which.

DETAILED DESCRIPTION OF THE PREFERRED EMBODIMENT

Figure 1:
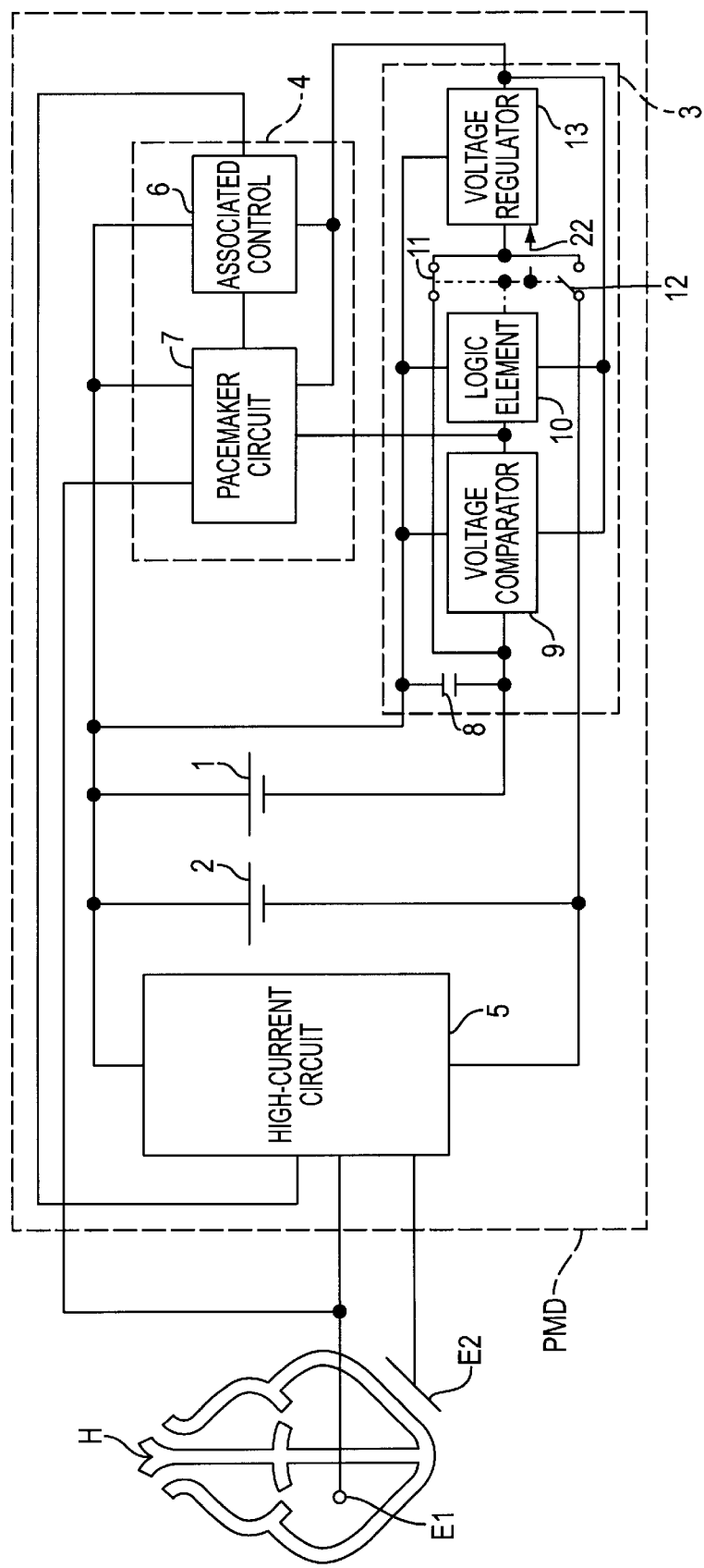
FIG. 1 shows a simplified block diagram of an implantable, combination defibrillator/pacemaker.

FIG. 1 shows the assemblies of an implantable, combination pacemaker/defibrillator PMD that are essential for explaining the embodiment of the invention; the remainder of the design corresponds to known devices. A 3-V Li/I battery having a capacity of 680 mAh to 2.5 V discharge voltage with the dimensions 12×32×7 mm, or 2.7 cm$^3$, is used as the first battery 1 for the pacemaker/defibrillator. A 6-V Li/MnO$_2$ battery having a capacity of $\geq$350 mAh for pulse operation and the dimensions 18×32×12.5 mm, or 7.2 cm$^3$, is provided as the second battery 2. In an alternate embodiment, the cathode element of the second battery may be composed of a mixture of MnO$_2$ and other metal oxides.

The Li/I battery 1 supplies the control circuit with sufficient energy for at least 4.85 years, assuming a current consumption of 16 µA. Until this time, the second battery 2 can emit the energy for at least 12 annual individual shocks of 2.1 mAh ($\approx$120 mAh) each. A capacity of $\approx$230 mAh, which suffices for 16 months of pacemaker operation and an additional 16 individual shocks of 2.1 mAh each, remains in the second battery 2. Thus, the pacemaker/defibrillator PMD having the battery arrangement 1, 2 (hybrid battery) has a minimum service life of 6.2 years.

As can be seen from FIG. 1, the two batteries are connected to the inputs of a current-supply element 3, whose output supplies a control circuit 4. The second battery is additionally connected to a high-current circuit 5. In the illustrated implantable defibrillator, this circuit includes circuits for charging the shock capacitors and administering shocks (not shown in the figure). The associated control 6 is a component of the control circuit 4, in addition to a pacemaker circuit 7 known per se. The current-supply element 3 essentially comprises a capacitor 8 that is switched in parallel to the first battery 1, a logic element 10, two electronic switches 11 and 12, and a voltage regulator 13. Also disposed in the block 3 are the electronic components that effect the switching of the supply of the pacemaker circuit with respect to the battery components following a corresponding voltage drop.

In FIG. 1, the arrow 22 indicates that an additional switching signal is transmitted to the voltage regulator upon the actuation of the switches 11 and 12. In this instance, the voltage regulator is configured as a voltage transformer that has a charge pump. The current supply of the pacemaker component is adapted to the higher voltage of the defibrillator battery by means of a corresponding stepping up of the switching stages involved in the voltage transformation, or through a reduction in the number of clock cycles with a fixed number of stages. This prevents a reduction in the efficiency of the circuit that would cause energy to be converted into heat during a transition to a higher supply voltage. A person skilled in the art is familiar with corresponding charge-pump circuits.

Figure 2:
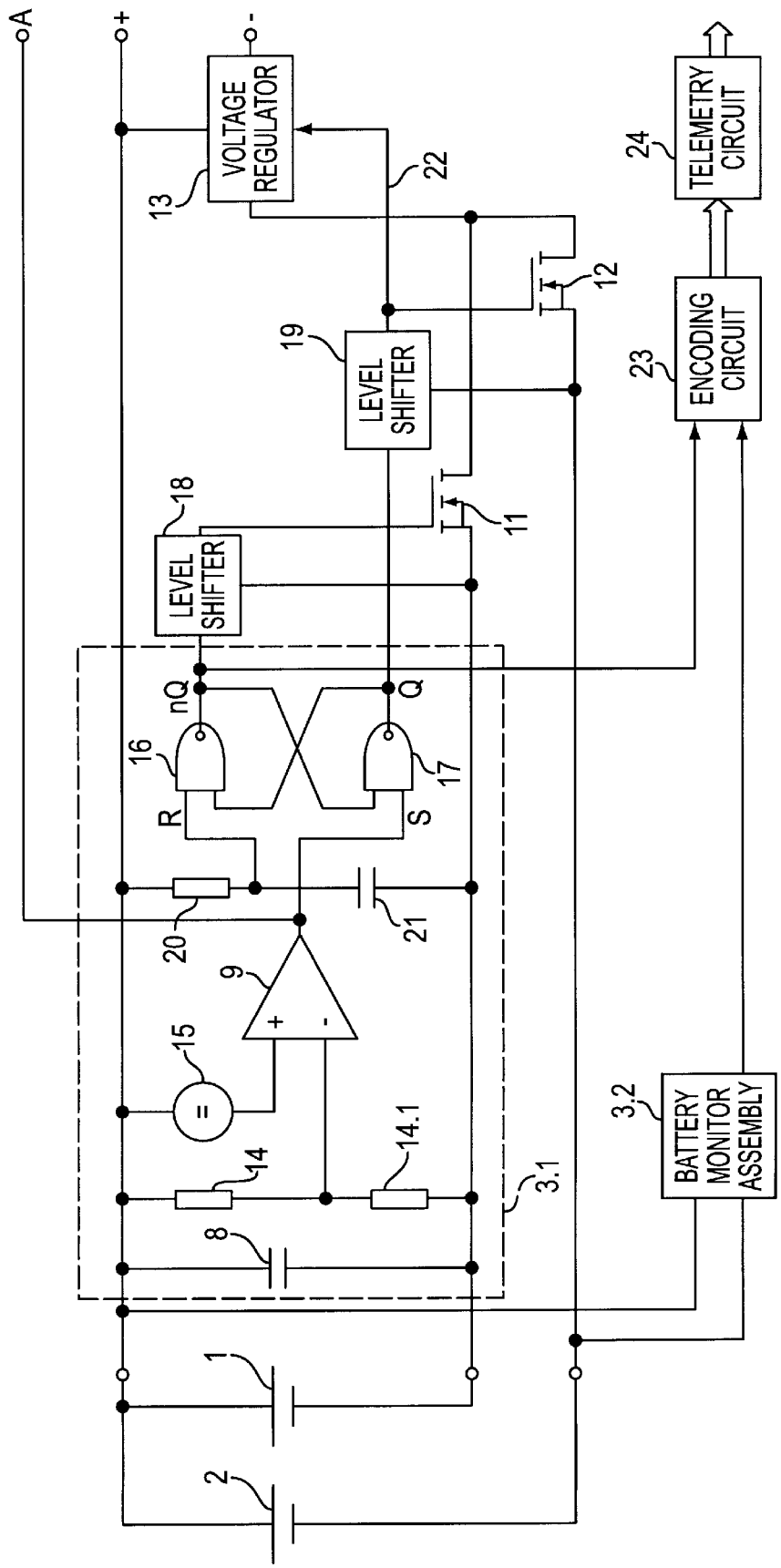
FIG. 2 shows a circuit diagram of the current-supply element of the device according to FIG. 1.

As can be seen from FIG. 2, the voltage of the first battery 1, which has been divided by means of a voltage divider 14, is compared to the voltage of a reference-voltage source 15 in the voltage comparator 9. The output signal emitted by the voltage comparator 9, which represents the result of the comparison, travels to both an output A, where it is available to the control circuit for an evaluation (for example, ascertaining the ERI), and the set input of a flip-flop comprising two NAND gates 16 and 17. Following the connection of the battery 1, the flip-flop is initially in the reset state, which is effected by an RC member comprising a resistor 20 and a capacitor 21. A transistor 11 acting as an electronic switch is connected by way of an output nQ and a level-shift circuit (level shifter) 18, that is, the input of the voltage regulator 13 is connected to the first battery 1. On the other hand, the electronic switch 12, which is configured as a transistor switch and actuated by way of the Q output of the flip-flop 16, 17 and a further level shifter 19, is blocked.

If the voltage of the first battery 1 drops below a predetermined value set by means of the reference-voltage source 15 and the voltage divider comprising the two resistors 14 and 14.1, the comparator 9 switches, and the flip-flop comprising the two cross-connected NAND gates 16, 17 is set. Consequently, the transistor 12 is switched on and the transistor 11 is blocked, and the input of the voltage regulator 13 is connected to the second battery 2. The circuit remains in this state even after the first battery 1 has recovered. The control circuit is subsequently supplied solely by the second battery 2.

In a modified embodiment, in which the circuit should return to the initial state after the voltage of the first battery 1 has increased again, the flip-flop is omitted, and the voltage comparator 9 is provided with a corresponding switching hysteresis. In this embodiment, the first battery 1 continues to contribute intermittently to the current supply of the control circuit following recovery, despite extensive depletion. Consequently, the energy of the first battery component can also be depleted if the component alone could no longer supply sufficient energy for maintaining the requirement of the first therapy component.

The buffering action of the capacitor 8 in the assembly 3.1 prevents a severe failure of the voltage of the first battery 1 when short-time current peaks occur, as is preferably the case when the pacemaker circuit 7 emits stimulation pulses. The voltage regulator 13 makes a constant voltage available to the downstream control circuit 4. The voltage comparator 9, the reference source 15 and the gates 16 and 17 are likewise supplied with this regulated voltage.

FIG. 2 is more detailed with respect to the embodiment shown in FIG. 1. In this case, not only is the output signal of the voltage comparator made available to the pacemaker circuit for triggering an end-of-life indication; it is additionally provided that a corresponding signal is telemetered for indicating to the physician that the normal service life of the pacemaker has ended and the switch must now be placed in some kind of reserve operation. To this end, the output signal of the flip-flop 16, 17 is supplied to an encoding circuit 23, which transmits the correspondingly-encoded signal to a telemetry circuit 24, which, as a transmitter, transmits the signal to an external receiver, not shown.

A further assembly 3.2 is provided, which essentially corresponds to the above-described assembly 3.1. Because the components used therein are identical, they need not be shown in detail. The residual energy of the battery 2 is monitored appropriately with the assembly 3.2, and the signal indicating the battery's imminent depletion is supplied to the encoding circuit 23, and is likewise outputted as information in the encoded signal. In this way, the physician can observe the different states of battery depletion from outside of the patient's body, and take the appropriate precautions. In a patient who only rarely requires a defibrillation shock, if it is indicated that the supply of the pacemaker circuit has been switched from battery 1 to battery 2, sufficient reserve time is still available. Only when the assembly 3.2 also emits a signal must a re-implantation be arranged.

The adaptation of the transmission ratio of the voltage-transformer circuit 13 by way of the line 22 was described above in conjunction with FIG. 1.

Of course, the design of the energy sources can also be effected in other relationships, depending on the concrete application, preferably with a switching point at six years and then six more months until the EOL (End Of Life).

It will be understood that the above description of the present invention is susceptible to various modifications, changes and adaptations, and the same are intended to be comprehended within the meaning and range of equivalents of the appended claims.

What is claimed is:

1. An implantable battery-operated, multi-function medical device comprising:

a first therapy assembly having a low current requirement;

a second therapy assembly having a large current requirement;

a first battery component adapted to be used with a device having a low current requirement and connected to said first therapy assembly;

a second battery component adapted to be used with a device having a large current requirement;

a sensor comprising a measuring device for detecting a measured value that is characteristic of the residual energy of the first battery component, taking into consideration the current and/or voltage requirement of the second therapy assembly, the measuring device having input and output sides, the input side of the measuring device being connected to an input side of the sensor, and being arranged to emit a control signal when the residual energy of the first battery component no longer suffices for low-current operation of the first therapy assembly, said measured value being the terminal voltage or the internal resistance of said first battery component; and a switching device connected to the output side of the measuring device and connecting the second battery component only to the second therapy assembly until the control signal is emitted, which indicates that the available residual energy of the first battery component is less than a predetermined residual energy value, upon which the switching device connects the second battery component to the first therapy assembly, while also leaving the second battery component connected to the second therapy assembly.

2. The multi-function device as defined in claim 1, wherein the measuring device for detecting a measured value comprises a comparator circuit that compares the measured value with a reference value and emits an output signal if a predetermined difference between the measured value and a comparison value has been exceeded.

3. The multi-function device as defined in claim 2, wherein the measured value is the terminal voltage, and the comparison value is a reference voltage.

4. The multi-function device as defined in claim 2, wherein the comparator unit, or a logic element disposed downstream thereof, has a hysteresis characteristic such that the first battery component is re-connected to the first therapy assembly when the terminal voltage increases again or the internal resistance drops again.

5. The multi-function device as defined in claim 2, wherein the switching device has a logic element that is connected to the output of the comparator unit, a first and a second electronic switch, the switches being actuated by way of the logic element, and a voltage regulator or transformer that is selectively connected on the input side to the first or second battery by way of the electronic switches.

6. The multi-function device as defined in claim 5, in which the first and second battery components have different terminal voltages, wherein the transmission ratio of the voltage transformer can be switched by means of the control signal such that the transmission ratio essentially corresponds to the ratio of the terminal voltage of the first battery component to the supply voltage of the first therapy assembly when the first therapy assembly is connected to the first battery component, and the transmission ratio essentially corresponds to the ratio of the terminal voltage of the second battery component to the supply voltage of the first therapy assembly when the first therapy assembly is connected to the second battery component.

7. The multi-function device as defined in claim 2, wherein the output of the comparator unit or the measuring device is connected to an input of a low-current control circuit.

8. The multi-function device as defined in claim 1, wherein the switching device includes a component for separating the first battery component from the first therapy assembly when connecting the second battery component to the first therapy assembly.

9. The multi-function device as defined in claim 1, wherein each of the first and second battery components comprises a hermetically-sealed battery on a lithium base.

10. The multi-function device as defined in claim 1, wherein the first battery component comprises a lithium/iodine battery having a high energy density, and wherein the second battery component comprises a lithium/manganese dioxide battery or a lithium/penta-vanadium battery having a high power density.

11. The multi-function device as defined in claim 10, wherein the cathode material of the second battery component comprises a mixture of manganese dioxide and other metal oxides.

12. The multi-function device as defined in claim 1, further comprising:
   a low-current control circuit for providing a current supply of the first therapy assembly; and
   control lines connecting the second therapy assembly to the low-current control circuit.

13. The multi-function device as defined in claim 1, said device being implantable in a patient's body and further comprising:
   a further sensor comprising a further measuring device for detecting a measured value that is characteristic of the residual energy of the second battery component, taking into consideration the current and/or voltage requirement of the first therapy assembly, the further measuring device having input and output sides, the input side of the further measuring device being connected to an input side of the further sensor, and being arranged to emit a further control signal when the residual energy of the second battery component only suffices for low-current operation of the first therapy assembly for a limited amount of time; and
   a telemetry device that is connected to the output of the further measuring device, and which transmits a telemetry signal to a receiver located outside of the patient's body, the signal being influenced by the further control signal.

14. The multi-function device as defined in claim 13, wherein the device includes an encoding device, which combines the output signal of the further measuring device with the output signal of the measuring device, and that the telemetry signal is influenced, in different ways, by both the control signal and the further control signal.

15. The multi-function device as defined in claim 1, wherein the device is adapted to be used in a combination pacemaker/defibrillator.

* * * * *